United States Patent [19]
Kobayashi et al.

[11] Patent Number: 5,401,469
[45] Date of Patent: Mar. 28, 1995

[54] PLASTIC OPTICAL BIOMATERIALS ASSAY DEVICE

[75] Inventors: Takeshi Kobayashi; Hiroyuki Honda, both of Nagoya; Ken-ichi Shimada, Ogaki, all of Japan

[73] Assignee: Ibiden Co., Ltd., Gifu, Japan

[21] Appl. No.: 238,782

[22] Filed: May 6, 1994

Related U.S. Application Data

[63] Continuation of Ser. No. 997,668, Dec. 28, 1992, abandoned, which is a continuation of Ser. No. 623,456, Dec. 18, 1990, abandoned.

[30] Foreign Application Priority Data

| Apr. 19, 1989 | [JP] | Japan | 1-97481 |
| Apr. 19, 1989 | [JP] | Japan | 1-97482 |
| Jul. 20, 1989 | [JP] | Japan | 1-185893 |
| Dec. 5, 1989 | [JP] | Japan | 1-314404 |

[51] Int. Cl.$^6$ .................................................. G01N 21/64
[52] U.S. Cl. ........................... 422/82.07; 422/68.1; 422/82.05; 422/82.08; 422/82.11; 436/164; 436/172; 436/532; 436/800; 436/805
[58] Field of Search ............... 422/68.1, 82.05–82.11; 436/164, 172, 531, 532, 535, 800, 805

[56] References Cited

U.S. PATENT DOCUMENTS

| 4,166,105 | 8/1979 | Hirschfeld | 424/8 |
| 4,447,546 | 5/1984 | Hirschfeld | 436/527 |
| 4,558,014 | 12/1985 | Hirschfeld et al. | 436/527 |
| 4,582,809 | 4/1986 | Block et al. | 436/527 |
| 4,666,862 | 5/1987 | Chan | 436/501 |
| 4,671,938 | 6/1987 | Cook | 422/57 |
| 4,716,121 | 12/1987 | Block et al. | 436/514 |
| 4,818,710 | 4/1989 | Sutherland et al. | 436/527 |
| 4,844,869 | 7/1989 | Glass | 422/68 |
| 4,857,273 | 8/1989 | Stewart . |  |
| 4,925,268 | 5/1990 | Iyer et al. | 422/82.06 X |
| 4,959,306 | 9/1990 | Kameda et al. | 435/7 |
| 5,019,350 | 5/1991 | Rhum et al. | 422/82.07 |
| 5,117,480 | 5/1992 | Yamamoto et al. | 385/145 |

FOREIGN PATENT DOCUMENTS

| 0184600 | 6/1986 | European Pat. Off. . |
| 58-30667 | 2/1983 | Japan . |
| 58-61468 | 4/1983 | Japan . |
| 59-81560 | 5/1984 | Japan . |
| 60-24450 | 2/1985 | Japan . |
| 60-36963 | 2/1985 | Japan . |
| 60-252265 | 12/1985 | Japan . |

(List continued on next page.)

OTHER PUBLICATIONS

Vo-Dinh et al, Anal. Chem., vol. 59, pp. 1226–1230 (1987).

Okubo et al., "Improvement . . . Modification", AIChe Journal, Jun. 1988, vol. 34, No. 6, pp. 1031–1033.

Koenig et al., "Raman . . . Surfaces", Materials Science and Engineering, 20 (1975) 127–135.

Shioji et al., "Adsorption . . . Glass", Wakayama Technical Higher Specialized School Reserach Memoir, No. 22 (1987), pp. 54–57.

(List continued on next page.)

Primary Examiner—James C. Housel
Assistant Examiner—Long V. Le
Attorney, Agent, or Firm—Birch, Stewart, Kolasch & Birch

[57] ABSTRACT

A reagent for biomaterials assay of (fluorescent dye)-$_n$—avidin—a compound having a plurality of reactive groups—a biomaterial, or a reagent in which avidin is bound to a compound having a plurality of reactive groups through biotin in the above, a plastic fiber optics necessary for utilizing this, an assaying device having a sensing portion utilizing this fiber optics and an assaying method of biomaterials by use of this reagent and device. The assay method can be used for an immunoassay of biomaterials such as antigens, antibodies, and enzymes contained in extremely minute amounts in blood or body fluid for medical diagnosis, and improves the detectable sensitivity to a great extent.

16 Claims, 6 Drawing Sheets

FOREIGN PATENT DOCUMENTS

| | | |
|---|---|---|
| 61-88155 | 5/1986 | Japan . |
| 61-191965 | 8/1986 | Japan . |
| 61-292044 | 12/1986 | Japan . |
| 62-66143 | 3/1987 | Japan . |
| 62-79333 | 4/1987 | Japan . |
| 62-79334 | 4/1987 | Japan . |
| 62-501102 | 4/1987 | Japan . |
| 62-123358 | 6/1987 | Japan . |
| 63-289001 | 11/1988 | Japan . |
| 64-47952 | 8/1989 | Japan . |

OTHER PUBLICATIONS

Yazawa et al., "Analysis . . . Glass", Yogyo–Kyokai–Shi (Journal of Ceramic Association, 95 (12) 1987, pp. 42–47.

Perry et al., "Structural . . . Phases", J. Chem. Soc. Faraday Trans, 1991, 87 (24), 3857–3862.

Perry et al., "Structural . . . Phases", J. Chem. Soc. Faraday Trans, 1991, 87 (5), 761–766.

H. A. Weetall (editor), "Immobilized . . . Peptides", Enzymology, 1975.

Marciniec et al., "Silane . . . 3–Aminopropyltriethoxysilane", International Polymer Science and Technology, vol. 18, No. 8, 1991, pp. T/62–T/67.

Chang et al., "The Structure . . . Surfaces", Journal of Colloid and Interface Science, vol. 74, No. 2, Apr. 1980, pp. 396–404.

Yazawa et al., "Reactivity . . . Compunds", Journal of Nippon Ceramics Association Treatise, 96(6), pp. 630–633 (1988).

Okuda et al., "Reaction . . . Compounds", Journal of Fermentation and Bioengineering, vol. 71, No. 2, pp. 100–105 (1991).

(mg/ml)

(mg/ml)

PLASTIC OPTICAL BIOMATERIALS ASSAY DEVICE

This application is a continuation of application Ser. No. 07/997,668, filed on Dec. 28, 1992, now abandoned, which is a continuation of prior application Ser. No. 07/623,456, filed on Dec. 18, 1990, now abandoned.

TECHNICAL FIELD

This invention relates to a reagent which can be used for assaying biomaterials in an immunoassay, a method for preparing the same, a plastic fiber optics necessary for the utilization thereof, an assay device having a sensing portion utilizing the fiber optics, and an assay method for biomaterials using the reagent and device.

BACKGROUND ART

There have been hitherto known various immunoassay methods as the method for detecting a trace component in the research fields such as medical diagnosis, clinical examinations, etc., and concerning this, various techniques have been proposed about reagents labelled with dyes, assay methods or devices.

1) Labelling reagent

For labelling reagents, there have been developed antigens or antibodies labelled with radioisotopes, luminous reagents or enzymes.

Among them, those having the highest sensitivity are those labelled with radioisotopes, but they cannot easily be handled. On the other hand, those labelled with enzymes are effective only for a part of substance. For this reason, sensitization of reagents labelled with luminous materials has been desired.

As such a high sensitivity reagent which can be used for luminous immunoassay, in Japanese Unexamined Patent Publication No. 61468/1983, an immunological reagent comprising an organic polymer having a plural number of luminescents bound to either one of an antibody or an antigen and an immunoassay by use thereof are proposed, and also, in U.S. Pat. No. 4,166,105, a detecting reagent of an analyte which is the primary reactant (antibody) capable of specifically reacting with a polymeric backbone possesing reactive functional group analyte, and has a large number of fluorophor molecules bound thereto is proposed, respectively. However, these reagents are not sufficient in the amount of the dye which can be bound. Therefore when an insensitive fluorescent dye excited at a long wavelength line is used, there is involved the problem that detectable sensitivity is not practical.

Also, in Japanese Unexamined Patent Publication No. 252265/1985, there is disclosed an assay method of a biologically active substance by using a reagent wherein a water-soluble organic polymer bound with a luminous reagent is bound to avidin. However, this reagent and method may probably reduce immunological activity because an antibody or an antigen is bound to avidin through biotin with small molecular weight, whereby a large amount of biotin is bound around the antibody or the antigen. Therefore it is necessary to make a treatment for prevention of this, and also there is the problem that a water-soluble polymer can be bound to avidin with difficulty due to steric hindrance.

2) Fiber optics used for luminous immunoassay

In luminous immunoassay, the method of exciting a fluorescent dye (luminous reagent) or transmitting fluorescence by utilizing a fiber optics is effective, and various techniques have been disclosed.

For using a fiber optics as the sensor, it is necessary to immobilize an antigen or an antibody onto a fiber optics, and as the techniques for this purpose, there are the membrane immobilization method which immobilize an antigen or an antibody onto a film such as cellophane, the entrapping method which seals an antigen or an antibody within pores of an acrylamide gel, etc. The former method has the problem of lowering sensitivity due to light scattering, and the latter has the problem of poor responsiveness. For such reasons, as the method for covalently bonding an antigen or an antibody directly to a fiber optics, in Analytical Chemistry, Vol. 59, No. 8, pp. 1226–1230, there is disclosed a method in which (3-glycidoxypropyl)trimethoxysilane (GOPS) which is a silane coupling reagent is allowed to react with the silanol groups on the surface of quartz fiber optics, subsequently this is treated with $HIO_4$ to introduce formyl groups onto the surface of the quartz fiber optics, and allowing amino groups of a protein with the formyl groups to effect immobilizing. However, this method is an effective only for quartz fiber, and cannot be used for plastic fiber optics. Plastic fiber optics are inexpensive in price, can be easily polished, are flexible and easy in handling, and hence it has been desired to have a method to bind a protein such as an antigen or an antibody to a plastic fiber.

Also, as the device using fiber optics, Japanese Unexamined Patent Publication No. 501873/1984 (U.S. Pat. No. 4,582,809) discloses an instrument for immunoassay and method, and Japanese Unexamined Patent Publications No. 123358/1987 and No. 501102/1987 (Switzerland Patent Application No. 5306/84–5) disclose fiber optic immunosensor, respectively. However, in these specifications, there is no description about the technique of labelling an antigen or an antibody highly sensitively, and for this reason, they can be utilized only for the case when a highly sensitive fluorescent dye as excited by Hg lamp, Xe lamp or Ar laser is employed as light source, and also there is the problem that the device is large in scale and expensive.

3) Assay method

There have also been made various proposals about the methods of immunoassay using luminous reagents. For example, in Japanese Unexamined Patent Publication No. 24450/1985, there is proposed a method for assaying biomaterials which measures the luminous intensity by the luminescence reaction of a luminescent binding avidin which is bound to an immuno-complex through biotin-avidin interaction. This method has avidin-biotin interaction interposed between the luminous reagent and an antibody or an antigen, but no other organic polymer interposed therebetween. Therefore, the amount capable of attaching luminescents is small, whereby there is the problem that insensitive luminescents can not be used. Also, as the reagent using biotin-avidin interaction, a labelled immunological material is proposed in Japanese Unexamined Patent Publication No. 30667/1983 (Switzerland Patent Application No. 6989/8101). However, this technique has the problem that the immunological material is labelled with an enzyme, and the treatment for measurement of enzyme activity is cumbersome.

DISCLOSURE OF THE INVENTION

The present inventors have studied intensively, and consequently thought of the fact that, in the method of assaying the concentration of a biomaterial, it is necessary for further enhancement of assay sensitivity to increase the amount of a fluorescent dye bound per one molecule of protein. For this purpose, biomaterials should be bound to a compound having a large number of reactive groups to bind a compound having a large number of fluorescent dye bound thereto to the respective reactive groups. Also, the inventor has successfully developed a sensing portion comprising fiber optics which can perform measurement by focusing the light emitted from the fluorescent dye efficiently, a device equipped therewith, and an assay method using this reagent and device.

Reagent for Biomaterials Assay

The reagent for biomaterials assay of the present invention is characterized in that a fluorescence labelled material is bound to a compound having a plurality of reactive groups, and a compound modified with a plurality of fluorescent dyes is bound to the reactive groups of said compound having a plurality of reactive groups.

The fluorescent dye as described in the present invention refers to a dye excited with a light, and does not mean a fluorescent dye which effects chemiluminescence or bio luminescence. The above-mentioned light is desirably a coherent light such as a laser beam.

The aforesaid reagent for biomaterials assay improves dramatically the detectable sensitivity by binding the compound having a plurality of reactive groups to most of which is bound a compound modified with a plurality of fluorescent dye, thereby increasing the amount attaching the fluorescent dye per biomaterial.

As the above reactive groups, an amino group, a thiol group, a hydroxyl group, a carboxyl group, a formyl group, etc. may be included, particularly an amino group is desired. The reason is because an amino group has relatively higher reactivity and the bond formed is stable.

The above reactive groups are desirably present 20 to 100000 groups per one molecule. The reason is because, if it is less than 20, no improvement of detectable sensitivity can be expected, while it is more than 100000, it is difficult to dissolve such a polymer in a solvent. The afresaid reactive groups are more preferably present 3000 to 6000 groups per one molecule, suitably 4000 to 5000 groups.

The compound having a plurality of reactive groups as described above is desirably a compound such as an aminoglucane or a polyaminopeptide. The reason is because 4000 to 5000 amino groups are present in these compounds.

As the above-mentioned aminoglucane, chitosan, polygalactosamine, polyneuraminic acid, etc. can be used, but it is preferred to use chitosan.

The above-mentioned polyaminopeptide is a polymer with amino acids having 2 or more amino groups polymerized through peptide bonds, and may include polylysine and others.

The compound modified with fluorescent dye to be used in the present invention is desirably a natural polymer having or a molecule with a molecular weight of 1000 or so, or more.

Natural polymers are desirably avidin, protein A, an antibody, a hormone, a hormone receptor, etc. which are available with relative ease.

For binding between the above-described compound having reactive groups and a biomaterial, and binding between the compound having a plurality of reactive groups and a compound modified with a plurality of fluorescent dyes, suitable cross-linking reagents can be used.

Also, the above-mentioned compound is preferably bound to the above-mentioned compound having a plurality of reactive groups through a substance which is specifically bound with said compound.

For example, when the above-mentioned compound is avidin, protein A, an antibody, a hormone or a hormone receptor, they are respectively bound to the above-mentioned compound having a plurality of reactive groups through biotin, an antibody, protein A, a hormone receptor, a hormone, and particularly the combination of "avidin-biotin" is preferred.

When the above combination of "avidin-biotin" is employed, fluorescent dyes are bound to the amino groups existing in a large number on the surface of avidin.

On the other hand, when the above combination of "protein A-antibody" is employed, fluorescent dyes may be bound to either of Protein A or antibody.

The above-mentioned avidin is a basic and crystalline albumin-like protein having a molecular weight of about 68000, and has selective and high affinity for biotin. Also, avidin is stable to heat, pH, chemical modification, etc. and moreover, it has an isoelectric point of 10 and has many amino groups on the molecular surface, whereby avidin is suitable for modification with fluorescent dyes.

The number of amino groups in avidin is 36, and among them some contribute to bonding with biotin, and therefore it is desired to bind 2 to 10 fluorescent dyes per one molecule of avidin.

Further, by labelling a complex of biotin—a compound having a plurality of reactive groups—biomaterials with the above-described modified avidin, a reagent for biomaterials assay of the present invention can be obtained.

The above-mentioned protein A is a protein having a molecular weight of 42000 comprising 5% of the cell wall of *Stapylococcus aureus*, has high affinity with immunoglobulins (antibody proteins), and therefore by labelling a complex of an antibody protein—a compound having a plurality of reactive groups—biomaterials with a protein A modified with fluorescent dyes, a reagent for biomaterials assay of the present invention can be obtained.

The above-mentioned protein A and antibody are both required to be unreactive with a biomaterial which is an analyte.

Thus, by binding a compound modified with a plurality of fluorescent dyes, a plurality of fluorescent dyes can be bound to one reactive group, whereby sensitivity can be dramatically improved.

In the present invention, it is necessary to excite fluorescent dyes with light.

The reason is because, by excitation with light, it is possible to perform a measurement which is by far safer as compared with immunoassay with radioisotope (radioimmunoassay) which is the prior art, and also cumbersome treatment of luminescence reaction in chemiluminescence or bioluminescence can be omitted to realize assay with higher precision and better reproducibility within a shorter time.

The above-mentioned light is desirably a laser beam of an LED beam (light emission diode), and said laser beam is desirably a He-Ne laser, or a semiconductor laser. The reason is because, the above-mentioned laser is smaller in size and also less expensive as compared with Xe lamp or Ar laser. When the above-mentioned semiconductor laser is employed, a laser beam of short wavelength can be emitted by combination with a SHG device (second harmonic wave generation device; a device which makes the wavelength of the light ½).

The fluorescent dye to be used in the present invention is desirably excited with light of 200 to 800 nm.

The reason is because, in the case of a wavelength shorter than the above wavelength, chemical bonds will be destroyed due to too high energy, while in the case of longer wavelength than said range, quantum yield of fluorescence is unpractically too low.

As the above-mentioned fluorescent dye, coumarin derivatives such as umbelliferone, etc., polycyclic aromatic derivatives, rhodamine isothiocyanate, fluorescein isothiocyanate, cyanine dyes, phycobiliproteins, dansyl derivarives, o-phthalaldehyde, etc. can be employed, and cyanine dyes are particularly preferred.

Cyanine dyes refer to those represented by the structure having heterocycles-containing azonium ion bound with a methyne chain, for example:

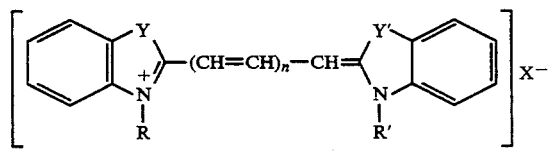

(wherein Y and Y' represent O, S, Se, —NH— or —CH=CH—, R and R' represent an alkyl group such as methyl, ethyl and propyl, or a carboxylalkyl group such as carboxyethyl, X represents a halogen atom, and n is a natural number of 0 to 3).

These cyanine dyes can be excited with a He-Ne laser (633 nm) or a semiconductor laser with the shortest wavelength presently emitted (638 nm).

Therefore, as compared with the case of employing an Ar laser or an Xe lamp, or the case of using a semiconductor combined with an SHG device, miniaturization and cost reduction can be effected.

As the above-mentioned cyanine dye, particularly the cyanine dyes represented by the formula (1) may be preferably employed:

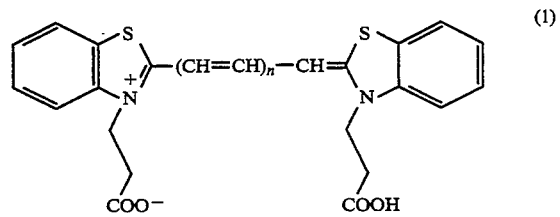

wherein n represents 0, 1, 2 or 3. Particularly preferably, n is 2.

Since labelling with fluorescent dyes is effected for one having bioactivity, it is required that the reaction should be completed within a short time under mild conditions so far as possible, and the label can be bound to reactive groups without side reactions. For this purpose, dyes of carbocyanine series represented by the above formula (I) having carboxylic groups outside of the conjugated system as the functional group may be preferably employed.

Also, as the above-mentioned cyanine dyes, those shown below can be also employed.

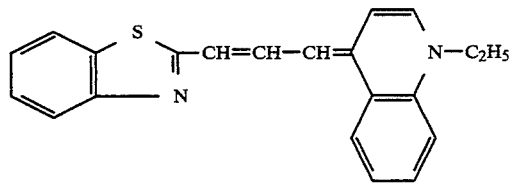

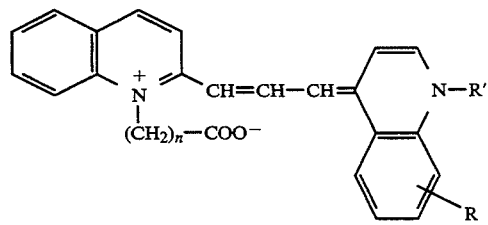

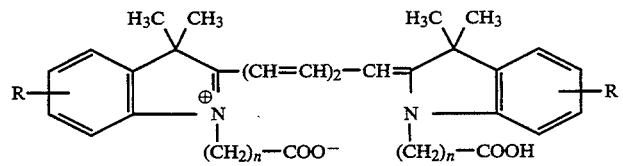

-continued

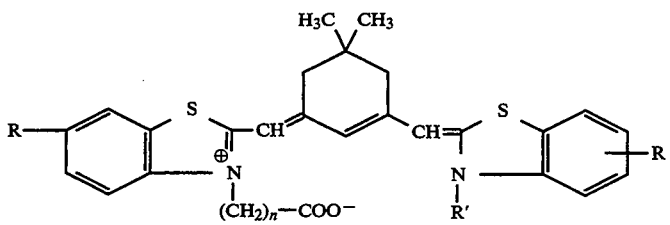

The biomaterials to be used in the present invention may include saccharides, proteins, etc., but particularly proteins are desired.

As the biomaterials comprising the above-mentioned proteins, antigens, antibodies, enzymes, hapten or enzyme inhibitors are desired.

The reagent for biomaterials assay of the present invention is desirably excited in the form bound to a fiber optics during assay.

Plastic Fiber Optics

The plastic fiber optics of the present invention is required to be a plastic fiber optics having reactive groups capable of covalently bonding a substance specifically binding the above-described reagent for biomaterials assay on the core surface.

The reason why the above-mentioned fiber optics is made of a plastic is because a plastic fiber optics has the characteristics that it is low in cost, can be worked more easily by polishing, and can be made larger in core diameter as compared with a glass fiber optics, whereby more dose can be transmitted, and also flexibility can be maintained even the core diameter may be made larger. Particularly, in the case of a fiber optics made of a polymethyl methacrylate, it is highly trasmittable in the wavelength region at around 560 to 650 nm.

The density of the above-mentioned reactive groups is desirably $1.0 \times 10^{10}$ to $6.0 \times 10^{13}$ groups/cm$^2$. The reason is because, if the density is lower than the above range, the absolute number of the reactive groups on the surface of plastic fiber optics becomes fewer, whereby assay sensitivity will be unpractically lowered, while if it is higher than the above range, transmittance of fluorescence emitted by fluorescent dyes into the fiber optics will become very poor (see FIG. 7: the case of polymethyl methacrylate).

Further, the density of the above-mentioned reactive groups is preferably $3.0 \times 10^{12}$ to $4.0 \times 10^{13}$ groups/cm$^2$, suitably $1.5 \times 10^{13}$ to $3.5 \times 10^{13}$ groups/cm$^2$. The reason is because, if the density is higher than the above range, the distance between the reactive groups becomes shorter, whereby reproducibility will begin to be lowered due to steric hindrance of the reagent for biomaterials assay as described above.

The plastic constituting the above plastic fiber optics is required to be a material which does not adsorb the biomaterials and has good light transmittance, and, for example, there can be used polystyrene, polyacrylate, polyester, polyacrylamide, polyvinyl alcohol, polyethylene terephthalate, polycarbonate, or copolymers of these, etc.

The above-mentioned plastic fiber optics is desirably composed mainly of a resin having a structure reactive with a cross-linking reagent. The reason is because a crosslinking reagent for introduction of reactive groups into the surface of the fiber optics can be readily reacted.

As the structure reactive with the above-mentioned crosslinking reagent, an ester bond, an amide bond, an ester group, a carboxylic group, a formyl group, an amino group, a hydroxyl group, an epoxy group, a thiol group, etc. are desired, but an ester structure such as an ester bond or an ester group is preferred.

As the light-transmittancy resin having a structure or a functional group reactive with the above-mentioned crosslinking reagent, a polyacrylate or a polyester is preferred.

The above-mentioned acrylate polymer is one having an ester structure among acrylic acid resin, which is a resin comprising a polymer of an ester derivative of acrylic acid, methacrylic acid, etc., specifically a polymer such as methyl acrylate, ethyl acrylate, methyl methacrylate and the like. Also, among the above-mentioned acrylate polymers, one particularly preferably employed in the present invention is polymethyl methacrylate. This is because polymethyl methacrylate is better in light transmittance as compared with other resins.

Whereas, as to the technique of binding a protein onto the surface of a plastic fiber optics, an example in which an antigen, an antibody were bound onto the surface of fiber optics made of nylon with the use of a cross-linking reagent is described in Japanese Unexamined Patent Publication No. 501873/1984 (U.S. Pat. No. 4,582,809). Also, although this is not a fiber optics, in Japanese Unexamined Patent Publication No. 129841/1981, there is described a technique which binds a protein onto the surface of a cell made of a polymethyl methacrylate or a nylon used in spectrophotometry.

However, the former technique employs fiber optics made of nylon which is low in light transmittance, and when the present inventors have tested it, transmission loss through the nylon fiber is great, whereby high sensitivity assay as intended by the present inventors could be done with difficulty.

On the other hand, the latter technique binds a protein onto a cell used in spectrophotometry, which is not a technique for immobilizing onto fiber optics.

The plastic fiber optics to be used in the present invention may be also a copolymer of a monomer such as methyl acrylate, ethyl acrylate, methyl methacrylate, etc. with a monomer such as styrene, etc.

As the above-mentioned reactive groups on the fiber optics surface, there may be included a formyl group, a carboxylic group, an amino group, a hydroxyl group, an epoxy group, a thiol group, an isocyanate group, an isothiocyanate group, etc., preferably a formyl group. The reason is because, while the substance covalently bonded to the fiber of the present invention is a biomaterial and mild reaction conditions are required which do not lower its activity, a formyl group reacts readily with the above-mentioned biomaterial, particularly the amino group of a protein.

The method for preparing the plastic fiber optics of the present invention is described below.

When the resin of the plastic fiber optics has no structure reactive with cross-linking reagents, functional groups are introduced into the resin, while when it has a structure reactive with a cross-linking reagent, functional groups are introduced into said structure portion through the reaction with an appropriate cross-linking reagent.

For the above-mentioned cross-linking reagent, it is desired to use a polyfunctional compound and, for example, there may be employed dialdehydes such as glutaraldehyde, succinic dialdehyde, adipoaldehyde, etc., N,N'-ethylene bismaleimide, N,N'-o-phenylene dimaleimide, bisdiazobenzene, or diisocyanates such as hexamethylene diisocyanate or diisothiocyanates and so on.

As a specific introduction method using the cross-linking reagent as described above, for example, when formyl groups are to be introduced into fiber optics made of polystyrene, the benzene ring, which is the side chain, is nitrated, then reduced to be converted into an amino group, which can be in turn reacted with glutaraldehyde to introduce a formyl group.

In the present invention, the most preferred plastic fiber optics for biomaterials assay is the form having formyl groups on the core surface of a plastic fiber optics composed mainly of a resin having an ester structure.

The above-mentioned plastic fiber optics for biomaterials assay may be prepared by reacting a nucleophile having a formyl group as the polyfunctional compound onto the exposed core surface of the plastic fiber optics, thereby introducing formyl groups into the core surface.

As the nucleophile having a formyl group mentioned above, a reagent represented by the formula (2) is preferred Formula:

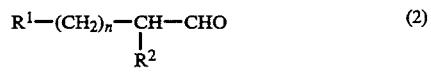

(wherein $R^1$ and $R^2$ each represent a hydrogen atom, an alkyl group or a formyl group, and n represents an integer of 0 to 5).

As the reagent represented by the above formula (2), glutaraldehyde and succinic aldehyde may be included.

The reagent of the formula (2) reacts nucleophilically with the ester group of a resin (polymethyl methacrylate in the following reaction scheme) as shown in the following reaction scheme.

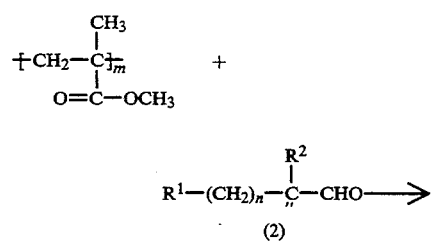

-continued

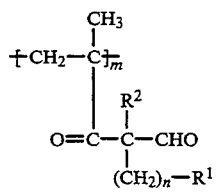

In the case of the reaction with the above-mentioned crosslinking reagent, it is desired that the core surface should be exposed by stripping the clad layer of the fiber optics.

The reason is because generally fiber optics has only a diameter of 1 mm, and the diameter of the core section about 0.97 mm (sectional area is 0.739 $mm^2$) and therefore for introducing many active groups, it is necessary to increase the core surface area by stripping the clad layer.

The end face of the fiber optics as described above is desirably polished. The above-mentioned polishing is preferably done using an alcohol as the lubricant.

The nucleophile having formyl group as described above is desirably prepared by adding and dissolving a base such as KOH, etc., an alcoholic organic solvent such as ethanol, etc., an ethanolic solution of a Ni salt such as $NiSO_4$, and a nucleophile having formyl group.

The concentration of a base such as KOH as mentioned above may be preferably 50 to 100 mM.

The reason for adding the above-mentioned Ni salt is because the Ni salt stimulates the reaction, and at the same time, prevents oxidation of formyl group and addition of OH group.

By dipping the core portion of the plastic fiber optics as described above into the reaction reagent as described above, the reaction is carried out to an ester structure, and it is desired to adjust the reaction temperature appropriately.

After the reaction treatment as mentioned above, the reaction product is washed with water, and dipped in an acid such as HCl, whereby the acetalated alcohol is eliminated to give an plastic fiber optics having formyl group bound thereto (see the following reaction scheme).

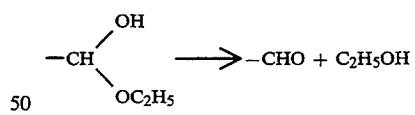

Sensing Portion for Assay

The sensing portion for biomaterials assay of the present invention is required to covalently bond a substance specifically binding with an analyte to the reactive groups of the plastic fiber optics as described above.

The substances specifically binding with the above-mentioned analyte are desirably a protein, and antigens, antibodies, enzymes, hapten, enzyme inhibitors, etc. may be conceivable.

When the reactive group of the plastic fiber optics as described above is formyl group, it is desirable to react a substance specifically binding with a substance to be assayed and then perform an immobilizing treatment. The reason is because, when no immobilizing treatment is performed, the substance specifically binding with an analyte will be readily eliminated through the reversible reaction.

The above-mentioned immobilizing treatment is described below by referring to the case when a protein is chosen as the substance specifically binding with the above-mentioned analyte.

First, when the plastic fiber optics having formyl groups introduced therein is dipped in a protein solution, the formyl group reacts with the amino group of the protein, whereby the binding site becomes imino group. After this is washed with water, by treatment with a reducing agent of an appropriate concentration, such as $NaBH_4$, the imino group is reduced to be inactivated, thereby immobilizing the protein.

(See the following reaction scheme. The resin is a polymethyl methacrylate).

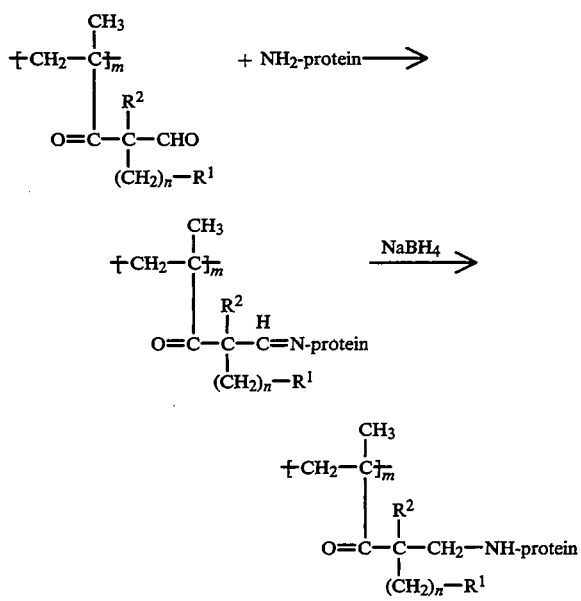

The sensing portion of the present invention may be also covered with a flow cell 5 as shown in FIG. 1, or alternatively of the opposing type as shown in FIG. 3, or also of the reflection type equipped at the tip end with a mirror as shown in FIG. 2.

In the case of the above-mentioned opposing type, excitation light is permitted to enter from the side opposed to the tip end and fluorescence is transmitted through the fiber optics 3 mounted with the sensing portion. On the other hand, in the reflection type, excitation light is permitted to enter by transmitting through the fiber optics 3 mounted with the sensing portion, and excitation light is reflected against the mirror 12 at the tip end and transmits through the above fiber optics 3.

Method for Preparing Reagent for Biomaterials Assay

The reagent for biomaterials assay of the present invention can be prepared according to various organic chemical reactions, but for preparation of the protein modified with a plurality of fluorescent dyes, fluorescent dyes and a protein are subjected to the reaction, and the residue after removal of the solvent from the reaction product is suspended in a buffer of pH 2 to 7 to remove the unreacted dyes by separation.

This is because, in the above-mentioned buffer of pH 2 to 7, the protein labelled with fluorescent dyes is dissolved, but the non-reacted fluorescent dyes not, whereby they can be easily separated from each other.

When the pH of the above-mentioned buffer is 2 or lower, the protein will undergo hydrolysis, while when the pH is 7 or higher, fluorescent dye will be dissolved.

The pH of the above-mentioned buffer is desirably 4.9 to 7.0, particularly 6.5±0.5 is preferable when preparing an avidin modified with cyanine dyes.

The above-mentioned fluorescent dye is desirably an acidic fluorescent dye showing good solubility in a basic buffer.

The above-mentioned fluorescent dye is desirably one which is excited with a laser beam.

As the above-mentioned fluorescent dye, cyanine dyes, fluorescein isothiocyanate, etc. as described above are employed.

For the proteins in the present invention, various proteins such as neocarzinostatin, enzymes, hormones, etc. may be conceivable, but it is desirably a basic protein (a protein with $PI \geq 7$). The reason is because the above-mentioned basic protein shows good solubility in the above-mentioned buffer of pH 2 to 7, even if hydrophobic fluorescent dyes may be bound thereto.

As the above-mentioned basic protein, avidin is preferred.

The reaction between the fluorescent dyes and the protein as described above may be carried out by use of a carbodiimide reagent such as dicyclohexylcarbodiimide and di-ptoluoylcarbodiimide, etc. to condense the amino group of the protein with the reactive group of the fluorescent dye.

The reaction solvent may be one which can dissolve the fluorescent dyes and the protein, and the reaction may be carried out in an organic solvent such as methanol, ethanol, methylamine, ethylamine, diethylamine, triethylamine, or a solvent such as a basic aqueous solution.

The reaction may be stopped, if necessary, by use of an acetic acid, etc. so that the reaction may not proceed so far as to cause the reaction between the OH group or SH group of the protein and the fluorescent dye to occur, thereby inactivating the reaction specificity possessed by the protein (antigen-antibody reaction, or reactivity with biotin when the protein is avidin).

After completion of the reaction, the solvent is distilled away in vacuo to dryness, and the residue is dissolved in a buffer of pH 2 to 7.

Since the unreacted fluorescent dyes are not dissolved, fluorescent dyes can be easily separated by an appropriate separation means.

As the means for separating unreacted dyes, they can be removed by subjecting to centrifugation, followed by passing of the supernatant through a tube packed with glass wool.

Next, out of the reagents for biomaterials assay of the present invention, one containing two kinds of specifically binding compounds, namely the compound A and the compound B, with a biomaterial bound to a compound having a plurality of reactive groups, the compound B being bound to the reactive groups of said compound having a plurality of reactive groups, and the compound A modified with a plurality of fluorescent dyes being bound to said compound B (for brevity, hereinafter called fluorescent dyes—compound A—compound B—compound having a plurality of reactive groups—biomaterials) is desirably prepared according to the method as described below.

That is, the compound B is allowed to react with most of the reactive groups of the compound having a plurality of reactive groups to modify the compound having a plurality of reactive groups with the compound B, then a biomaterial is reacted therewith to form a complex of compound B—compound having a plurality of reactive groups—biomaterial, followed by the reaction with the compound A modified with fluorescent dyes to prepare the fluorescent dyes—compound A—compound B—compound having a plurality of reactive groups—biomaterial complex.

The reason why the above preparation method is desired is because, if the reaction order is changed, side reactions will occur to lower the yield.

In the preparation method as described above, the combination of the compound A and the compound B is desirably a protein and a compound specifically binding with said protein, and specific examples are preferably avidin and biotin, protein A and an antibody, an antibody and protein A, etc., particularly optimally the combination of avidin and biotin.

The reactions are described in more detail.

A compound having a plurality of reactive groups, for example, chitosan (I) has a large number of amino groups in the molecule, and when chitosan (I) is allowed to react with biotin (II) in a basic solution in the presence of a dehydrating reagent such as a water-soluble carbodiimide (CHMC) and N-hydroxysuccinimide, biotin forms acid amide bonds with most of the amino groups of chitosan to give a biotinylated chitosan (III). The biotinylated chitosan (III) is allowed to react with the protein which is the biomaterial by using the same dehydrating reagent as mentioned above to give a biotinylated chitosan (IV) having the protein bound to the remaining free amino groups of chitosan (I)

On the other hand, the avidin (V) modified with fluorescent dye can be obtained by allowing the carboxylic groups of fluorescent dyes such as cyanine dyes to react with the amino groups of avidin which is the protein, according to the same method as described above.

Next, when the biotinylated chitosan (IV) having the above-mentioned protein bound thereto is allowed to react with the avidin (V) modified with the above-mentioned fluorescent dye, avidin can be bound to biotin selectively with very high affinity to give the fluorescence labelled protein (VI) of the present invention.

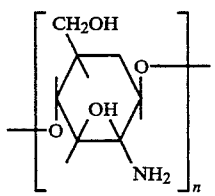

Chitosan (I)

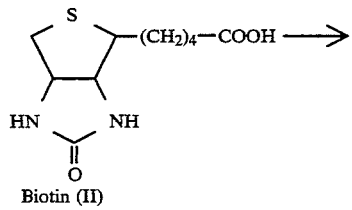

Biotin (II)

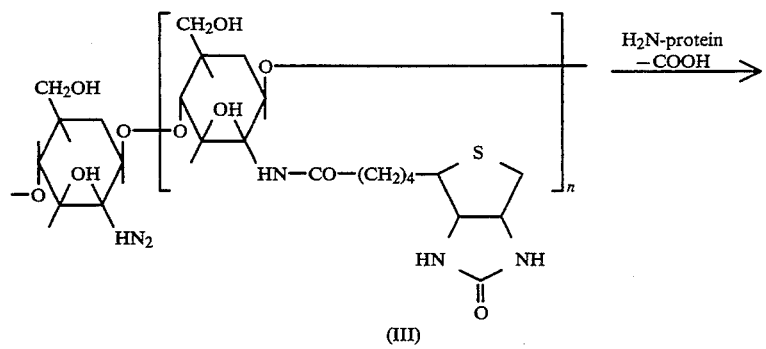

(III)

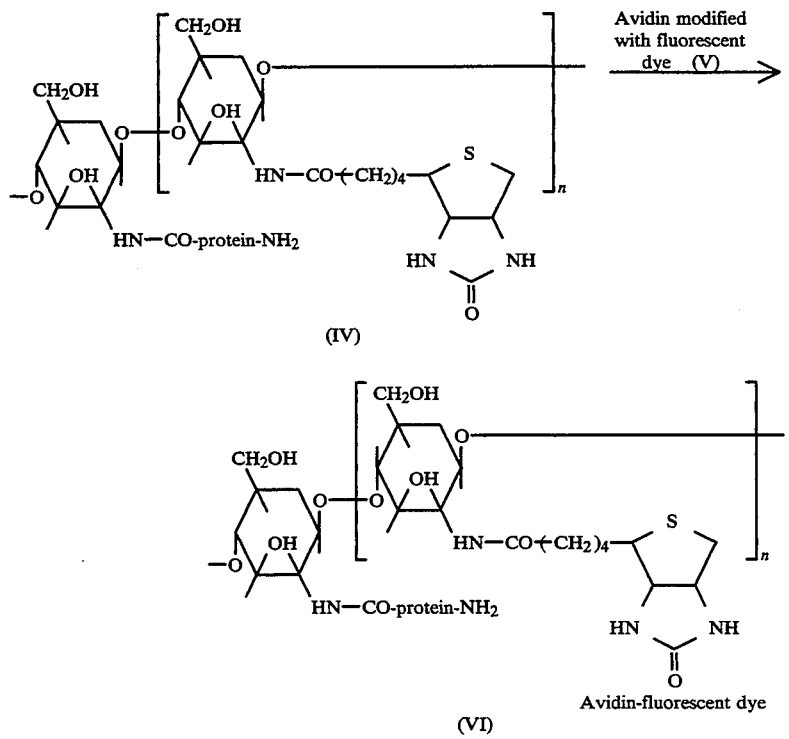

(IV)

(VI)

Avidin-fluorescent dye

The carboxylic group of the above-mentioned cyanine dye can be easily amide-bonded to the amino group of avidin by condensation in a conventional manner in an organic solvent by using a dehydrating condensing reagent such as dicyclohexylcarbodiimide. After completion of the reaction between the cyanine dye and avidin, non-reacting materials are preferably removed so far as possible, and can be removed, for example, by dialysis, centrifugation, gel filtration or filtration using a filter material.

The acid amide bond formed by bonding biotin to chitosan has characteristic fluorescence peaks at around the respective wavelengths of 450 nm, 300 nm and 490 nm, when the excitation wavelength is 225.5 nm at pH 6.

And, since there is a linear relationship between the difference in fluorescence intensity between 458 nm and 300 nm and the concentration of acid amide bonds, a standard curve of chitosan can be prepared by utilizing this characteristic, and the biotinylated amount can be estimated from the amount of the acid amide bonds.

Biomaterials Assay Method

The assay methods by use of the reagent for biomaterials assay of the present invention are to be described.

The assay method using the reagent for biomaterials assay of the present invention may be practiced according to the methods as described below.

1) An assay method, which comprises reacting specifically a complex comprising a fluorescent dye—avidin—biotin—an analyte or a substance reacting specifically with an analyte with a substance specifically reacting with an analyte or an analyte on a fiber optics, and then measuring the fluorescence by excitation with light.

2) An assay method, which comprises reacting specifically an analyte or a substance specifically reacting with an analyte to which biotin is bound with a substance specifically binding with an analyte or an analyte on fiber optics, then reacting an avidin modified with fluorescent dye with the reaction product to form a complex through bonding of avidin—biotin on the fiber optics, and thereafter measuring the fluorescence by excitation with a light.

3) An assay method, which comprises reacting specifically a reagent comprising an analyte or a substance specifically reacting with an analyte bound to a compound having a plurality of reactive groups and a compound modified with a plurality of fluorescent dye bound to the reactive groups of said compound having a plurality of reactive groups with a substance specifically binding with an analyte or an analyte on a fiber optics, and then measuring the fluorescence by excitation with a light.

4) An assay method, which comprises, when the two kinds of substances specifically bound to each other are defined as the compound A and the compound B, binding specifically a reagent comprising an analyte or a substance specifically reacting with an analyte bound to a compound having a plurality of reactive groups and the compound B bound to said reactive group with a substance specifically binding with an analyte or an analyte on fiber optics, then reacting the compound A modified with a fluorescent dye with the reaction product to form a complex through bonding of the compound A—the compound B on the fiber optics, and thereafter measuring the fluorescence by excitation of the fluorescent dye with light.

The above assay method 1) is to be described.

In the above assay method 1), it is necessary to use a complex comprising fluorescent dye—avidin—biotin—analyte or substance specifically binding with analyte as the reagent.

The reason why the above-mentioned reagent is used is because when an analyte or a substance specifically reacting with an analyte is directly labelled with a fluorescent dye, the amount of the fluorescent dye labelled is limited, and also there is a fear that the binding active sites of the analyte or the substance specifically reacting with the analyte may be damaged.

For this reason, via the above-mentioned avidin—biotin, much fluorescent dye can be bound without damaging the active binding sites.

The above-mentioned reagent is specifically reacted with a substance specifically binding with the analyte or the analyte on the fiber optics, and then excited with light.

Excitation is effected on the fiber optics, because exciting light and fluorescence can be transmitted by the fiber optics to enable efficient assay.

The above-mentioned fluorescent dye is desirably a cyanine dye.

The reason is that a cyanine dye can be excited with a He—Ne laser (633 nm) or a semiconductor laser (638 nm), whereby the device can be made smaller in size and reduced in cost.

For binding of the above-mentioned cyanine dye to avidin, it is required that the reaction should be completed under mild conditions so far as possible within a short time, and the reactive groups can be bound without side reactions, and for that purpose, a carbocyanine series dye represented by the following formula having carboxyl groups outside of the conjugated system as the functional group may be preferably used.

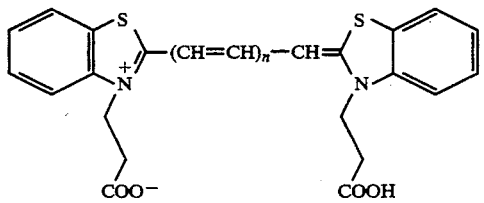

(wherein n represents 0, 1, 2 or 3).

For obtaining an avidin modified with a cyanine dye, the carboxy group of the cyanine dye and the amino group of a protein may be allowed to form an amide bond in an organic solvent in the presence of a dehydrating condensing reagent such as a carbodiimide. In this case, non-reacting dyes are separated.

The light source to be used in the present invention is desirably a laser beam or an LED beam.

The above-mentioned assay method may be broadly classified into the competitive format assay and the sandwich method.

The above-mentioned competitive format assay is a method in which an analyte sample and a reagent of a known concentration comprising fluorescent dye—avidin—biotin—analyte are mixed, the fiber optics having a substance specifically binding with the analyte immobilized thereon is dipped therein to carry out specifically the reaction, and then fluorescence is measured by excitation with light. In the case of the above-mentioned competitive format assay, to the fiber optics are bound the analyte sample and the reagent comprising fluorescent dye—avidin—biotin—analyte according to the respective ratios of concentration.

Therefore, if the concentration of the analyte sample is high, the bound amount of the reagent comprising fluorescent dye—avidin—biotin—analyte is reduced relatively to be lowered in fluorescence intensity, whereby the slope of the standard curve of concentration—fluorescence intensity becomes negative.

In the above-mentioned sandwich method, fiber optics which are immobilized with a substance specifically binding with an analyte are placed in an analyte sample. To the above-mentioned fiber optics is bound the analyte according to its concentration. The fiber optics having said analyte bound is dipped in a solution of a reagent comprising fluorescent dye—avidin—biotin—a substance specifically binding with an analyte. To the above-mentioned fiber optics is bound a reagent comprising fluorescent dye—avidin—biotin—a substance specifically binding with the analyte.

In the above-mentioned sandwich method, to the fiber optics is bound a reagent comprising the same number of fluorescent dye—avidin—biotin— a substance specifically binding with the analyte as that of the analyte sample.

Therefore, if the concentration of the analyte sample is high, the bound amount of the reagent comprising fluorescent dye—avidin—biotin— a substance specifically binging with the analyte is increased to increase fluorescence intensity, whereby the slope of the standard curve of concentration—fluorescence intensity becomes positive.

Next, the assay method 2) is to be described.

The above-mentioned assay method 2) has basically the same effect as the assay method 1), but in this method, it is necessary to first specifically react an analyte or a substance specifically reacting with the analyte to which biotin is bound with a substance reacting specifically with the analyte or the analyte on the fiber optics, and then reacting an avidin modified with fluorescent dyes with the reaction product.

The reason is because, since the avidin modified with fluorescent dyes is bound finally, lowering in fluorescence intensity accompanied with hydrolysis or oxidation of fluorescent dyes can be prevented to effect assay of high reproducibility.

The above-mentioned fluorescent dye is desirably a cyanine dye.

The light source to be used in the present invention is desirably a laser beam or an LED beam.

The above-mentioned assay method can be broadly classified into the competitive format assay and the sandwich method.

The above-mentioned competitive format assay is a method in which an analyte sample and a reagent of a known concentration comprising biotin-analyte are mixed, fiber optics having a substance specifically binding with the analyte immobilized thereon is placed therein to react specifically, then an avidin modified with fluorescent dyes is bound with the reaction product followed by excitation with light and assay. In the case of the above-mentioned competitive format assay, to the fiber optics are bound the analyte sample and the reagent comprising fluorescent dye—avidin —biotin—analyte according to the respective ratio of concentration.

Therefore, if the concentration of the analyte sample is high, the amount of the reagent comprising fluorescent dye —avidin—biotin—analyte is relatively reduced to lower fluorescence intensity, whereby the slope of the standard curve of concentration—fluorescence intensity becomes negative.

In the above-mentioned sandwich method, fiber optics to which a substance specifically binding with the analyte is immobilized is placed in an analyte sample.

To the above-mentioned fiber optics is bound the analyte according to its concentration. The fiber optics bound with said analyte is dipped in a solution of a reagent comprising biotin—a substance specifically binding with an analyte. To the above-mentioned fiber is bound the reagent comprising biotin—the substance specifically binding with analyte. To the fiber optics bound with the reagent comprising the above-mentioned biotin—the substance specifically binding with analyte is bound an avidin modified with fluorescent dyes.

In the above-mentioned sandwich method, to the fiber optics is bound the substance specifically binding with the same number of fluorescent dye—avidin—biotin— analyte as that of the analyte sample.

Therefore, if the concentration of the analyte sample is high, the bound amount of fluorescent dye—avidin—biotin —the substance specifically binding with an analyte is increased to increase fluorescence intensity, whereby the slope of the standard curve of concentration—fluorescence intensity becomes positive.

Next, the assay method 3) is to be described.

The above-mentioned assay method 3) is required-to use a reagent in which an analyte or a substance specifically reacting with an analyte is bound to a compound having a plurality of reactive groups, and a compound modified with a plurality of fluorescent dyes is bound to the reactive groups of said compound having a plurality of reactive groups.

By use of the above-mentioned reagent, the amount of the fluorescent dyes bound per a biomaterial can be increased to improve dramatically the detectable sensitivity.

The above-mentioned fluorescent dye is desirably a cyanine dye.

Also, the above-mentioned compound modified with a plurality of fluorescent dyes is preferably avidin, and desirably bonded to the reactive groups of the compound having a plurality of reactive groups via biotin.

Also, the compound having a plurality of reactive groups is desirably selected from aminoglucans, and chitosan is particularly preferred.

Also, the light source for exciting the above-mentioned fluorescent dye is desirably a laser beam or an LED beam.

The above assay method may be classified broadly into the competitive format assay and the sandwich method.

The above-mentioned competitive format assay is a method in which an analyte sample and a reagent in which an analyte is bound to a compound having a plurality of reactive groups and a compound modified with a plurality of fluorescent dyes is bound to the reactive groups of said compound having a plurality of reactive groups are mixed, fiber optics having a substance specifically binding with the analyte immobilized thereon is dipped therein to react specifically, and then fluorescence is measured by excitation with a light. In the case of the above-mentioned competitive format assay, to the fiber optics are bound the analyte sample and the above-mentioned reagent according to the respective ratios of concentration.

Therefore, if the concentration of the analyte sample is high, the bound amount of the above-mentioned reagent is relatively reduced to lower the fluorescence intensity, whereby the slope of the standard curve of concentration fluorescence intensity becomes negative.

In the above-mentioned sandwich method, fiber optics to which a substance specifically binding with an analyte is immobilized is placed in an analyte sample. To the above-mentioned fiber optics is bound the analyte according to its concentration. The fiber optics bound with said analyte is placed in a solution of a reagent in which a substance specifically binding with the analyte is bound to a compound having a plurality of reactive groups, and a compound modified with a plurality of fluorescent dyes is bound to the reactive groups of said compound having a plurality of reactive groups.

In the above-mentioned sandwich method, the same number of assay reagents as that of the analyte sample are bound to the fiber optics.

Therefore, if the concentration of the analyte sample is high, the bound amount of the reagent assayed is increased to increase fluorescence intensity, whereby the standard curve of concentration - fluorescence intensity becomes positive.

Next, the assay method 4) is to be described.

In the above-mentioned assay method, when two kinds of substances binding specifically to each other are defined as the compound A and the compound B, it is required that first, a reagent in which an analyte or a substance specifically reacting with an analyte is bound to a compound having a plurality of reactive groups and the compound B being bound to said reactive groups is reacted specifically with the substance specifically binding with the analyte or the analyte on the fiber optics, and then the reaction product to react with the compound A modified with fluorescent dyes.

By using such a method, the amount of the fluorescent dyes per the analyte can be increased, and yet lowering in fluorescence intensity accompanied with hydrolysis or oxidation of the fluorescent dye can be prevented to perform assay of high reproducibility.

The above-mentioned fluorescent dye is desirably a cyanine dye.

The above-mentioned compound A and compound B may be preferably respectively combinations of avidin-biotin, protein A-antibody, antibody-protein A, particularly the combination of avidin-biotin is preferred.

The antibody to be used as the above-mentioned compound A or compound B is required to undergo no specific reaction with the analyte.

The above-mentioned compound having a plurality of reactive groups is preferably selected from aminoglucans, and chitosan is particularly preferred.

The light source for exciting the above-mentioned fluorescent dye is desirably a laser beam or an LED beam.

The above assay method may be classified broadly into the competitive format assay and the sandwich method.

The above-mentioned competitive format assay is a method in which an analyte and a reagent of a known concentration comprising an analyte bound to a compound having a plurality of reactive groups with the compound B being bound to said reactive groups are mixed, fiber optics having a substance binding specifically with the analyte immobilized thereon is dipped therein to carry out specifically the reaction, and the compound A modified with fluorescent dye is bound to the reaction product, and fluorescence is measured by excitation with a light. In the case of the above-mentioned competitive format assay, to the fiber optics are bound the analyte sample and the above-mentioned reagent corresponding to the respective ratios of concentration.

Therefore, if the concentration of the analyte sample is high, the bound amount of the reagent bound is reduced relatively to lower the fluorescence intensity, whereby the slope of the standard curve of concentration—fluorescence intensity becomes negative.

In the above-mentioned sandwich method, fiber optics having a substance specifically binding with the analyte sample immoblized thereon is dipped in the analyte sample. To the above-mentioned fiber optics is bound the analyte sample according to its concentration. The fiber optics bound with said analyte is placed in a solution of a reagent in which the substance specifically binding with the analyte is bound to a compound having a plurality of reactive groups and the compound B is bound to said reactive groups. To the above-mentioned fiber is bound the reagent. The compound A modified with fluorescent dyes is bound to the fiber optics bound with the reagent in which the substance specifically binding with the above-mentioned analyte is bound to a compound having a plurality of reactive groups and the compound B is bound to said reactive groups.

In the above-mentioned sandwich method, the same number of reagents as that of the assay sample are bound to the fiber optics.

Therefore, if the concentration of the sample to be measured is high, the bound amount of the reagents is increased to increase fluorescence intensity, whereby the slope of the standard curve of concentration—fluorescence intensity becomes positive.

Biomaterials Assay Device

In the following, the device is to be described.

The device of the present invention is a device for assaying biomaterials by utilizing the above-described biomaterials assay reagent in which biomaterials are bound to a compound having a plurality of reactive groups, and a compound modified with a plurality of fluorescent dyes is bound to the reactive groups of said compound having a plurality of reactive groups.

The device of the present invention comprises at least the constitution as mentioned below, namely a sensing portion having a small size light source and fiber optics for transmitting the exciting light or fluorescence, and a substance specifically binding with an analyte immobilized on the core surface exposed on its one end face; a mechanism for taking out only the fluorescence excited at the sensing portion; and a photocounter for measuring the fluorescence intensity excited at the sensing portion.

The reason why the above-mentioned fiber optics is used is because exciting light and fluorescence can be transmitted by the fiber optics, whereby efficient assay can be done without optical loss.

The above-mentioned fiber optics is desirably made of a plastic. The reason is because plastic is lower in cost and can be used more easily.

The above-mentioned plastic fiber desirably has a structure reactive with a cross-linking reagent. The reason is because a biomaterial can be covalently bonded via a crosslinking reagent to form a sensing portion.

The above-mentioned structure reactive with a cross-linking reagent is desirably an ester structure.

As the plastic mentioned above, (meth)acrylate resins such as polymethyl methacrylate or polyester resins are preferred.

Further, the sensing portion of the present invention is required to be bound with an biomaterial assay reagent comprising a biomaterial bound to a compound having a plurality of reactive groups and a compound modified with a plurality of fluorescent dyes bound to the reactive groups of said compound having a plurality of reactive groups during assay.

By binding such a reagent, high sensitivity assay is possible.

The above-mentioned fluorescent dye is desirably a cyanine dye. The reason is because the above-mentioned cyanine dye can be excited with a He-Ne laser beam (630 nm) or a semiconductor laser with the shortest wavelength presently emitted (638 nm), and therefore it is not necessary to use a large scale and expensive Xe lamp or Ar laser, or an expensive SHG device (element which makes the wavelength of light by $\frac{1}{2}$), whereby an inexpensive and small size device can be obtained.

The above-mentioned sensing portion is desirably capable of desorbing from the fiber optics transmitting excited light or fluorescence through a connector.

As the above-mentioned connector, the guide rail type is preferred as shown in FIG. 3.

The light source of the device of the present invention is required to be of small size and low cost. And it is desirably a He—Ne laser, a semiconductor laser, a laser comprising a combination of a semiconductor laser and an SHG device, or an LED (light emission diode).

The mechanism for taking out only the above-mentioned fluorescence is considered to be a half mirror or a filter, but desirably a filter.

The reason is because when a half mirror is employed, a space for setting an optics is required, whereby miniaturization can be effected with difficulty. The above-mentioned half mirror is used when the sensing portion is the reflection type, while the above-mentioned filter is used primarily when the sensing portion is the opposing type.

For this reason, the above-mentioned sensing portion is preferably the opposing type.

BEST MODE FOR PRACTICING THE INVENTION

In the following, Examples of the present invention are shown.

Example 1

(1) In 100 μl of water were dissolved 3 mg of $Na_2CO_3$ and 4 mg of biotin.

(2) Subsequently, the solution obtained above in (1) was added into 2 ml of a 1.8 μM chitosan solution.

(3) After addition of 100 μl of water, 50 mg of CHMC (aqueous solution carbodiimide). Further, under stirring, the reaction was carried out at room temperature for 5 hours to overnight.

(4) The reaction was terminated by dropping 3 drops of acetic acid.

(5) Subsequently, 4 ml of a mixture of 0.3 g/ml of $Na_2CO_3$ and 0.3 g/ml of NaCl was added to precipitate biotinylated chitosan.

(6) After the precipitates were recovered by a centrifugal machine, the precipitates were washed with 0.3 g/ml of NaCl and 0.1 g/ml of $Na_2CO_3$ buffer.

(7) The precipitates obtained in the above (6) were dialyzed with 10 ml of 10 mM potassium-phosphate buffer (pH=7) overnight at 4° C. to obtain biotinylated chitosan.

(8) Into a suspension of the above biotinylated chitosan were added an anti-IgG (antibody Y) solution and CHMC to carry out the reaction at 4° C. overnight. After completion of the reaction, dialysis was carried out for 12 hours, followed further by removal of non-reacting materials by use of an anion exchange column, to give a biotinylated chitosan having the antibody bound thereto.

(9) Avidin (1 mg) and 0.2 ml of triethylamine were dissolved in 1 ml of ethanol. Subsequently, 2 mg of NK1160 (a cyanine dye of the above formula (1) wherein n=2; available from Japanese Research Institute for Photosensitizing Dyes Co.,Ltd.) was added to be sufficiently dissolved to prepare a solution. Further, 14 mg of dicyclohexylcarbodiimide was added into the above solution, and the reaction was carried out at room temperature for 4 hours.

(10) After completion of the reaction, ethanol and triethylamine were removed under reduced pressure by an evaporator.

(11) The residue formed in the process of the above (10) was suspended in 2 ml of a 0.01M acetate buffer (pH=6.5), then centrifuged at 5000 rpm for 10 minutes by use of a centrifugal machine, the supernatant was collected and subjected again to centrifugation to obtain a solution of avidin modified with NK1160.

(12) The tip end of an plastic fiber optics of 1 mm in diameter composed mainly of polymethyl methacrylate (available from Mitsubishi Rayon Co., Ltd., trade name: Esca) was dipped in ethyl acetate, wiped off, and 1 cm of the clad layer was stripped, followed by washing with water. Subsequently, the end surface of the fiber optics was polished with a polishing film by use of ethanol as the lubricant.

(13) In 0.5 ml of water was dissolved 10 mg of $NiSO_4$, and then 2.5 ml of ethanol was added. At this time, white precipitations were formed, which were centrifuged at 3000 rpm, and the supernatant was collected to give an Niethanol solution.

Into 0.4 ml of a 50 mM potassium hydroxide-ethanol solution was added 0.1 ml of the Ni-ethanol solution, followed further by addition of 50 μl of a 50% glutaraldehyde solution to give a reaction solution.

(14) The plastic fiber optics of the above (12) was dipped in the reaction solution prepared in the above (13) at 50° C. for 10 minutes, and then washed with water.

(15) It was then dipped in a 20 mM hydrochloric acid solution for 5 to 10 minutes, and then washed with water to introduce formyl group into the core portion surface of the plastic fiber optics.

FIG. 6(b) shows the relationship between treatment temperature and amount of an enzyme (protein) which can be immobilized when formyl groups are introduced into the surface of the fiber optics, and FIG. 6(a) shows the relationship between treatment temperature and transmittance of the fiber.

Also, FIG. 7 shows the relationship between density of the formyl groups on the fiber surface and light transmission loss.

The fiber optics made of polymethyl methacrylate is improved in light transmittance when subjected to heat treatment, but increased in density of bound formyl groups when the reaction temperature becomes higher, whereby light transmittance is lowered. For this reason, as shown in FIG. 6(a), the optimum temperature is around 50° C.

(16) 1 mg of a mouse IgG antigen 4 which is a monoclonal antibody to thermostable α-amylase produced by the genus *Bacillus* 16-3F strain was dissolved in a phosphate-buffered physiological saline (pH=7.5). In this solution was dipped an plastic fiber optics at 4° C. for 12 hours.

(17) The plastic fiber optics was taken out from the solution, washed with water, then dipped in a 1% $NaBH_4$ aqueous solution for 15 minutes and washed with water, whereby the mouse IgG antigen 4 was immobilized to give an antigen immobilized sensor.

(18) The plastic fiber optics prepared as described above was made the sensing portion.

(19) After the anti-mouse IgG (Y) solution of a known concentration was dipped in the sensing portion 5 prepared in (18), it was washed by passing through a phosphate-buffered physiological saline.

(20) Next, the sensing portion 5 was dipped in the biotinylated chitosan solution having an antibody bound thereto obtained in the above (8), and then washed by passing through a phosphate-buffered physiological saline.

(21) Next, after the solution of avidin modified with NK1160 obtained in the above (11) was dipped in the sensing portion 5, it was washed by passing through a phosphate-buffered physiological saline.

(22) Next, by means of the device of the present invention shown in FIG. 4, fluorescence was measured with a He—Ne laser system by use of a spctrophotometer 8.

(23) The same measurements as in the above (18) to (22) were repeated by varying the concentration of the antimouse IgG (Y), and the relationship between concentration of the anti-mouse IgG (Y) and fluorescence intensity was examined to prepare a standard curve. This is shown in FIG. 8(a). Also, response of the sensor is shown in FIG. 9.

From the standard curve, limit of detection was measured, and this is shown in Table 1.

Example 2

(1) According to the same methods as in Example 1 (1) to (18), the biotinylated chitosan solution having the antibody bound thereto, the avidin solution modified with NK1160, the antigen immobilized sensor and the sensing portion were prepared.

(2) An anti-mouse IgG (Y) solution of a known concentration and the biotinylated chitosan solution having the antibody bound thereto prepared in the above (1) were mixed at a ratio of 1:1, passed through the flow cell 5 shown in FIG. 1 and then washed by passing through phosphate-buffered physiological saline.

(3) Next, the avidin solution modified with NK1160 prepared in the above (1) was passed through the flow cell 5, and then washed by passing through phosphate-buffered physiological saline.

(4) Next, according to the same methods as in the foregoing Example 1 (22) and (23), the relationship between concentration of the anti-mouse IgG (Y) and fluorescence intensity was examined to prepare a standard curve. The standard curve is shown in FIG. 8(b).

From the standard curve, the limit of detection was measured, and this is shown in Table 1.

Example 3

(1) In 100 μl of water were dissolved 3 mg of Na$_2$CO$_3$ and 4 mg of an antibody protein.

(2) Subsequently, the solution obtained in the above (1) was added into 2 ml of a 1.8 μM β-1,4-polygalactosamine solution.

(3) After addition of 100 μl of water, 50 mg of CHMC (aqueous solution carbodiimide) was added. Further, under stirring, the reaction was carried out at 4° C. overnight.

(4) Subsequently, 4 ml of a mixture of 0.3 g/ml of Na$_2$CO$_3$ and 0.3 g/ml of NaCl was added to precipitate β-1,4-polygalactosamine having the antibody protein bound thereto.

(5) After recovery of the precipitates by a centrifugal machine, the precipitates were washed with 0.3 g/ml of NaCl and 0.1 g/ml of Na$_2$CO$_3$ buffer.

(6) The precipitates obtained in the above (5) were suspended in 10 ml of a 10 mM potassium-phosphate-buffered (pH =7), dialyzed at 4° C. overnight to obtain a β-1,4-polygalactosamine having the antibody protein bound thereto.

(7) Into a suspension of the above β-1,4-polygalactosamine having the antibody protein bound thereto, an anti-mouse IgG (Y) solution and CHMC were added to carry out the reaction at 4° C. overnight. After completion of the reaction, dialysis was carried out for 12 hours, and further non-reacting materials were removed by use of an anion exchange column to obtain a β1,4-polygalactosamine having the antibody protein bound thereto.

(8) One mg of protein A and 0.2 ml of triethylamine were dissolved in 1 ml of ethanol. Subsequently, 2 mg of NK1160 (available from Japanese Research Institute for Photosensitizing Dyes Co., Ltd.) was added and sufficiently dissolved to prepare a solution. Further, to the above solution was added 14 mg of dicyclohexylcarbodiimide, and the reaction was carried out at room temperature for 4 hours.

(9) After completion of the reaction, the solvent was removed by an evaporator.

(10) The residue formed in the process of the above (9) was suspended in 2 ml of a 0.01M acetate buffer (pH=6.5), subjected to separation by means of a centrifugal machine at 5000 rpm for 10 minutes, the supernatant was collected and again subjected to centrifugation to obtain a solution of the protein A modified with NK1160.

(11) The reaction between the β1,4-polygalactosamine having the antibody protein bound thereto obtained in the above (8) and the above protein A modified with NK1160 was carried out in a phosphate-buffered physiological saline at 4° C. to obtain a complex solution of cyanine dye—protein A—antibody protein—β1,4-polygalactosamine—antibody (Y).

(12) In Example 1 (13), by use of succindialdehyde in place of glutaraldehyde and by use of a fiber optics containing a polyester in place of the fiber optics made of the polymethyl methacrylate, the sensing portion shown in FIG. 1 was prepared according to the same methods as in Example 1 (12) to (18).

(13) An anti-mouse IgG (Y) solution of a known concentration and the complex solution of cyanine dye—protein A—antibody protein—β1,4-polygalactosamine—antibody (Y) obtained in the above (12) were mixed at a ratio of 1:1, passed through a flow cell 5 shown in FIG. 1, then washed by passing through phosphate-buffered physiological saline, followed by measurement of fluorescence by a spectrofluorophotometer 8 with a He—Ne laser optics by means of the device of the present invention shown in FIG. 5. By varying the concentration of the anti-mouse IgG (Y) and repeating the measurement in the same manner, the relationship between concentration of the anti-mouse IgG (Y) and fluorescence intensity was examined to prepare a standard curve. From the standard curve, the limit of detection was measured, and this is shown in Table 1.

Example 4

(1) According to the same methods as in Example 1 (1) to (8), a biotinylated chitosan solution having an antibody bound thereto was prepared.

(2) 1 mg of avidin and 1.8 mg of fluorescein isothiocyanate were dissolved in 5 ml of a basic solvent comprising 0.5M sodium carbonate—sodium hydrogen carbonate buffer (pH=9.0), and stirring was continued at 4° C. with cutting off of light to carry out the reaction for 20 hours.

(3) Subsequently, the reaction mixture was distilled the solvent away in vacuo by use of an evaporator.

(4) The residue was suspended in 5 ml of a 0.05M phosphate-buffered (pH=4.0).

(5) The suspension was centrifuged at 5000 rpm for 10 minutes to remove the non-reacting dye, and the supernatant was collected.

(6) The above operations of (3) and (4) were further repeated twice, and further the supernatant obtained was passed through a pipe filled with glass wool to remove the non-reacting dye to obtain an avidin modified with fluorescein isothiocyanate.

(7) According to the same methods as in Example 1 (12) to (18), an antigen immobilized sensor and a sensing portion were prepared.

(8) After an anti-mouse IgG (Y) solution of a known concentration was passed through the flow cell 5 shown in FIG. 1, it was washed by passing through phosphate-buffered physiological saline.

(9) Next, the biotinylated chitosan solution having an antibody bound thereto obtained in (1) was passed through the flow cell 5, and then washed with phosphate-buffered physiological saline.

(10) Next, the solution of the avidin modified with fluorescein isothiocyanate obtained in (6) was passed through the flow cell 5, and then washed by passing through phosphate-buffered physiological saline.

(11) Next, fluorescence was measured with the device of the present invention shown in FIG. 4 by use of a laser optics (wavelength 490 nm) comprising a semiconductor laser and a thin film waveguide type SHG device and a spectrophotometer 8.

(12) By varying the concentration of the anti-mouse IgG (Y), the same measurements as in the above-described (8) to (11) were repeated, and the relationship between concentration of the anti-IgG (Y) and fluorescence intensity was examined to prepare a standard curve.

From the standard curve, the limit of detection was measured, and this is shown in Table 1.

Example 5

This invention is basically the same as Example 1, but after treatment of (11), 4 ml of 0.17 g/ml of saturated sodium sulfate solution (solvent: 10 mM potassium phosphate-buffered, pH=7) was added, and the mixture was subjected to centrifugation at 2000 rpm for 10 minutes and left to stand at 4° C. for 1 hour.

The precipitates obtained were suspended in a 10 mM potassium phosphate-buffered.

Sodium sulfate crystals were removed by centrifugation, and the supernatant was dialyzed and concentrated before use.

From the standard curve, the limit of detection was measured, and this is shown in Table 1.

Example 6

Into the solution obtained in Example 1 (1), 50 mg of CHMC was further added to be dissolved therein, the solution was left to stand at 12° C. for 2 hours, and by use of this solution, the treatments of Example 1 (2) and thereafter were conducted. From the standard curve, the limit of detection was measured, and this is shown in Table 1.

Example 7

In this Example, polylysine was employed in place of chitosan in Example 1. The reaction conditions are similar to those in Example 1. From the standard curve, the limit of detection was measured, and this is shown in Table 1.

Example 8

(1) A solution of avidin modified with the NK1160 obtained according to the treatments of Example 1 (9) to (11) was obtained.

(2) The sensing portion of Example 1 was dipped in a mouse IgG (antigen) solution at 4° C. for 12 hours.

(3) Subsequently, after washing, treatment was carried out with 1% NaBH$_4$ to immobilize the antigen.

(4) The sensing portion was dipped in an anti-mouse IgG solution of a known concentration, and washed with a phosphate-buffered physiological saline.

(5) The sensing portion was dipped in a biotinylated antibody solution, followed by washing.

(6) Subsequently, the sensing portion was dipped in the solution of (1) and, after washing, measurement was conducted by the device in FIG. 1.

(7) By repeating such operations, the standard curve in FIG. 6(c) was prepared, from which the limit of detection was measured, and this is shown in Table 1.

Example 9

A detection reagent was prepared by the reaction between the solution of Example 7 (1) and a biotinylated antibody, and this reagent was mixed with an anti-mouse IgG solution of a known concentration at a ratio of 1:1, the sensing portion of Example 7 was dipped therein, measurements were conducted to prepare a standard curve, the limit of detection was measured therefrom, and this is shown in Table 1.

Example 10

(1) By applying treatments of Example 1 (9) to (11), a solution of avidin modified with NK1160 was obtained.

(2) The solution of the above (1) and a chitosan solution bound with an anti-IgG obtained in the same manner as in Example 1 (8) were mixed, glutaraldehyde was added to the mixture, and the mixture was heated at 50° C. in tile presence of carbodiimide to cross-link the amino groups of avidin and the amino groups of chitosan with glutaraldehyde, thereby obtaining a solution of NK1160—avidin—(glutaraldehyde)—chitosan—anti-IgG.

(3) A fiber optics made of a polystyrene was allowed to react with formic anhydride in the presence of aluminum chloride to introduce formyl groups into the phenyl groups of the polystyrene, and subsequently the reaction product was allowed to react with 1,6-hexanediamine in the presence of carbodiimide, followed by reduction with 1% NaBH$_4$.

Subsequently, a mouse IgG was subjected to dehydration condensation in the presence of a carbodiimide to prepare a sensing portion 5.

(4) By use of the solution of the above (2) and the sensing portion of the above (3), measurement was conducted according to the competitive format assay similarly as in Example 2.

From the standard curve, the limit of detection was measured, and this is shown in Table 1.

TABLE 1

| Example | Limit of detection (mg/ml) |
| --- | --- |
| 1 | $1.2 \times 10^{-4}$ |
| 2 | $2.0 \times 10^{-4}$ |
| 3 | $2.3 \times 10^{-4}$ |
| 4 | $3.1 \times 10^{-6}$ |
| 5 | $1.0 \times 10^{-4}$ |
| 6 | $1.1 \times 10^{-4}$ |
| 7 | $1.3 \times 10^{-4}$ |
| 8 | $1.0 \times 10^{-1}$ |
| 9 | $1.1 \times 10^{-1}$ |
| 10 | $2.1 \times 10^{-4}$ |

Example 11

Examples of the device of the present invention are shown in FIG. 1 to FIG. 5.

FIG. 1 shows a sensing portion having a structure which excludes the clad layer 2 of the surface layer portion of a fiber optics 1, having an antigen 4 bound to the core portion surface 3 exposed and also having the above core surface portion 3 surrounded with a flow cell 5.

FIG. 2 is a reflection type detection portion, having a mirror 12 provided at the tip end.

FIG. 3 shows the structure of the opposing type fluorescence detector. A fluorescence sensing portion (sensing chip) 9 is stopped with a guide 11 for optical axis matching, and absence of adhesion permits the fluorescence sensing portion 9 to be freely capable of desorbing, which is very convenient in practical application. The fluorescence sensing portion 9 is exchanged every time for measurement, and therefore is desirably a plastic fiber optics in view of the cost. Onto the above-mentioned plastic fiber optics, reactive groups are introduced according to various methods. The above-mentioned plastic fiber optics preferably have an ester structure such as polyacrylate ester, and when the above-mentioned fluorescence sensing portion is prepared with a plastic fiber optics, a compound having >CH—CHO structure is allowed to react with the ester group under alkaline conditions to introduce formyl group, and a protein such as antigen or antibody is bound to the formyl group.

The excited light is radiated from the fiber opposed to the detection surface.

In the device shown in FIG. 4, a laser beam enters from the plate side 10 to the fluorescence sensing portion 9, the incident light and fluorescence enter the plastic fiber having the guide 11, and only fluorescence is taken by the filter 7 and measured by the spectrophotometer 8.

FIG. 5 shows a device when employing a flow cell type detector.

Utilizability in Industry

The reagent for biomaterials assay of the present invention can be used for immunoassay of biomaterials contained in extremely minute amount such as antigen, antibody, enzyme, etc. in blood or body fluid for medical diagnosis, and due to large amount of fluorescent dye per one biomaterial, detectable sensitivity can be improved to great extent.

Also, the fiber optics for biomaterials assay can realize miniaturization, low cost and high sensitivity.

According to the assay method of the present invention by use of these biomaterials assay reagent and device therefor, simple assay can be realized within a short time, and therefore they can be utilized for diagnosis of diseases in clinical field, etc.

BRIEF DESCRIPTION OF THE DRAWINGS

In FIGS. 1 to 3, full arrow indicates a laser beam, and dotted arrow indicates a fluorescence.

Figure 1:
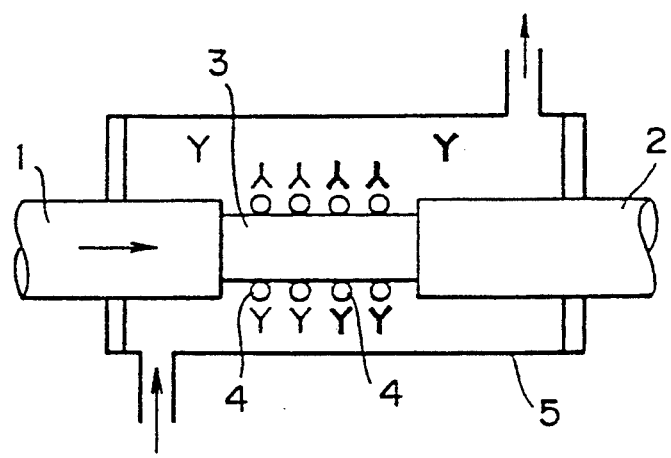
FIGS. 1 to 3 show fluorescence sensing portions according to the fluorescence labelling method.
Figure 2:
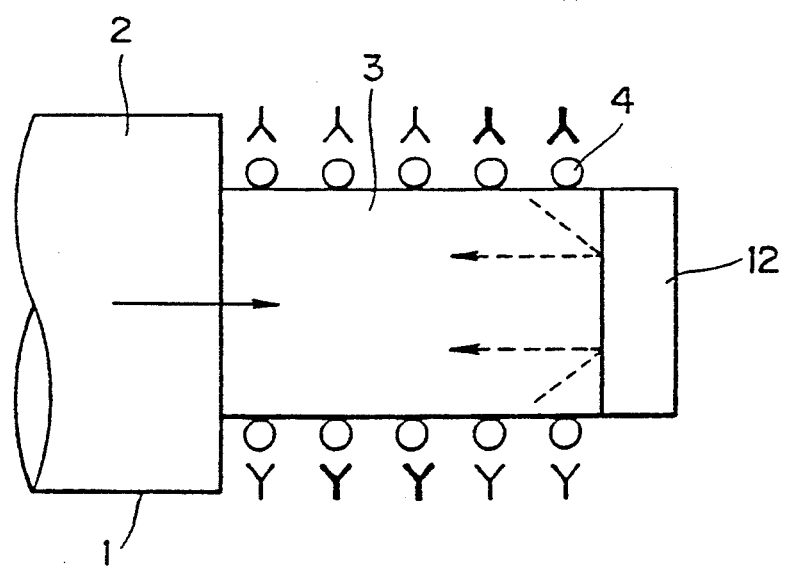
Figure 3:
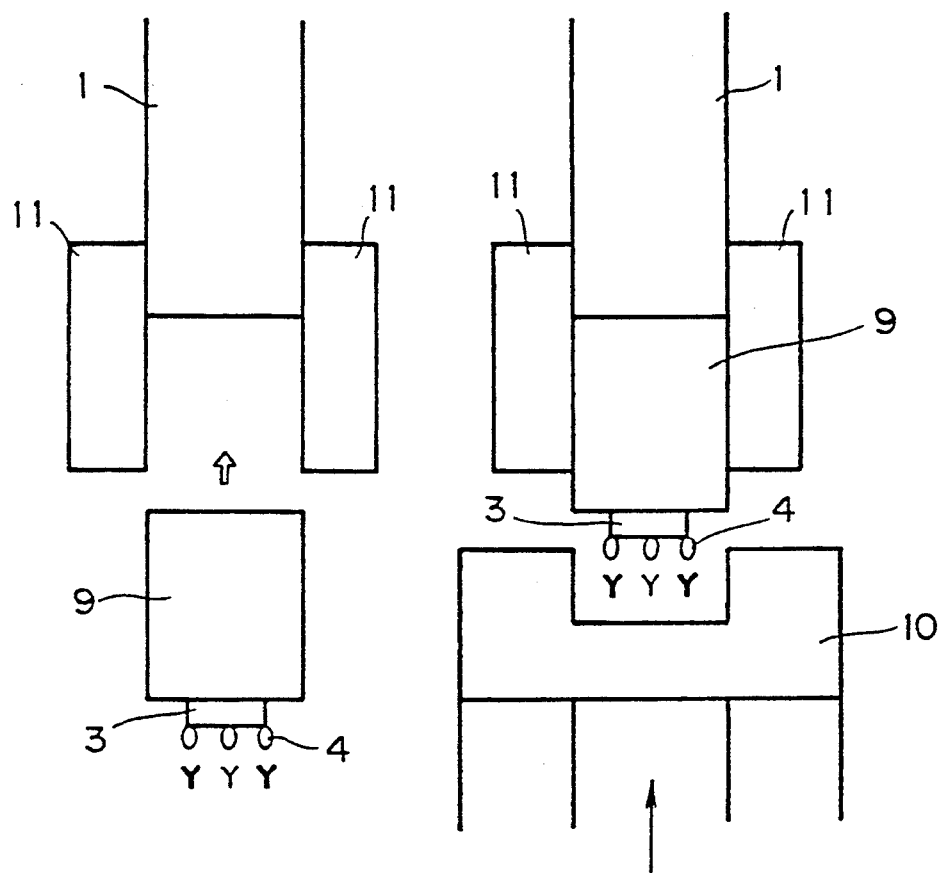
Figure 4:
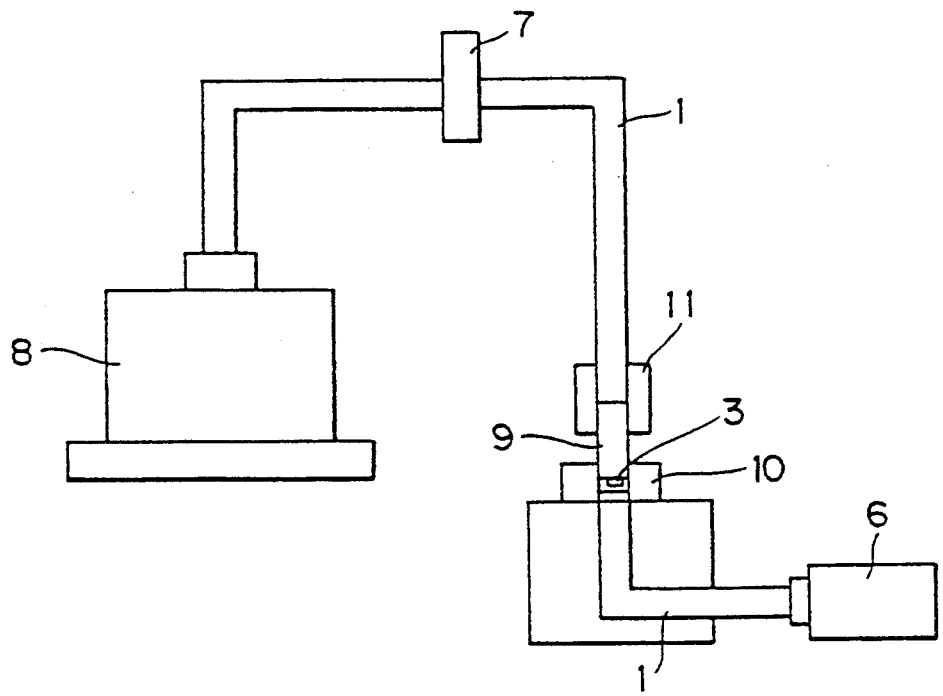
FIGS. 4 and 5 show fluorescence measurement systems by use of He—Ne laser or semiconductor laser.
Figure 5:
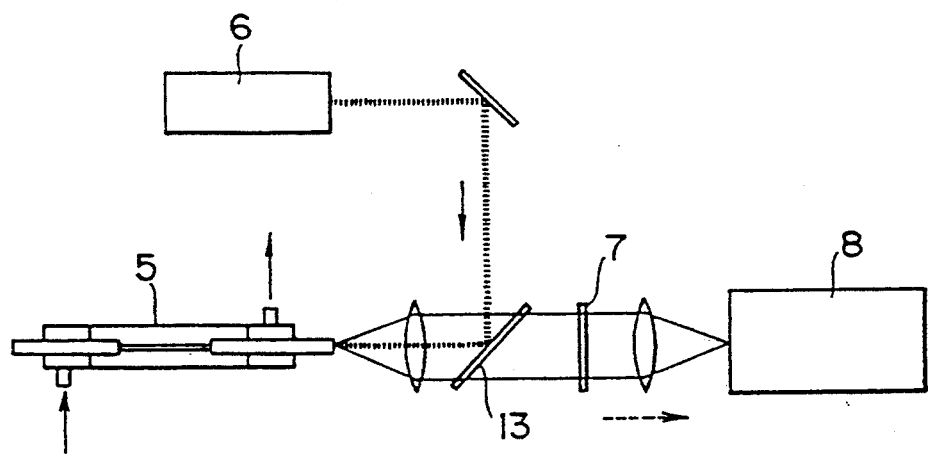
Figure 6:
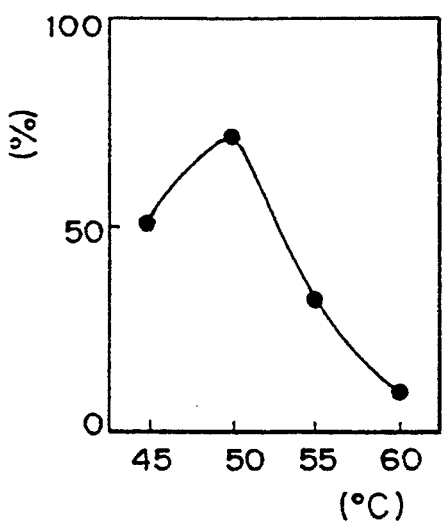
FIG. 6(a) shows the relationship between treatment temperature and light transmittance of fiber optics made of a polymethyl methacrylate.
FIG. 6(b) shows the relationship between treatment temperature and bindable enzyme amount. The axis of abscissa in Figures (a) and (b) indicate treatment temperature (C°), the axis of ordinate in Figures (a) indicates light transmittance of the fiber (%), the axis of ordinate in Figure (b) indicates amount of immobilized enzyme per area ($\mu g/cm^2$), the axis of abscissa in Fig. (c) indicates biotinylated antimouse antibody concentration (mg/ml), and the axis of ordinate indicates count number.
FIG. 6(c) shows the standard curve of biotinylated antimouse antibody concentration and fluorescence intensity.
Figure 6:
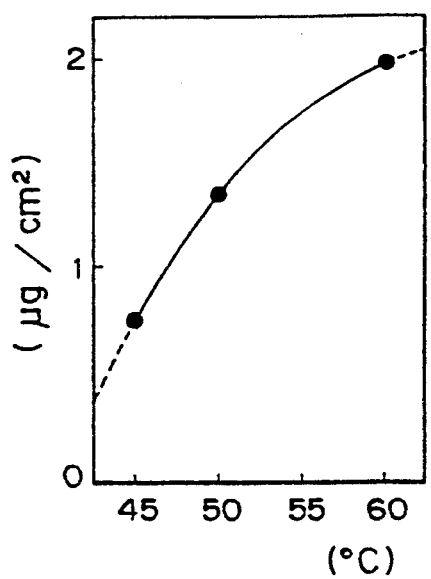
Figure 6:
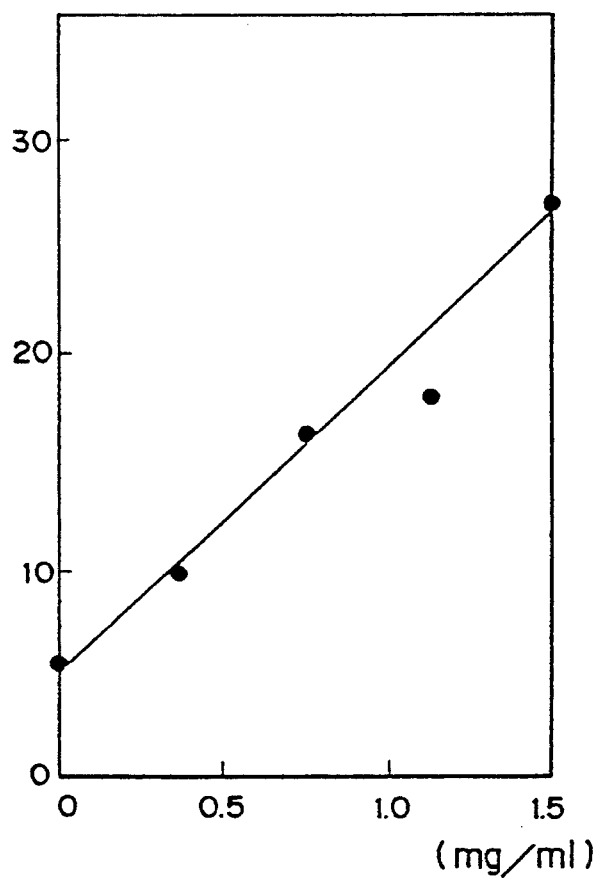
Figure 7:
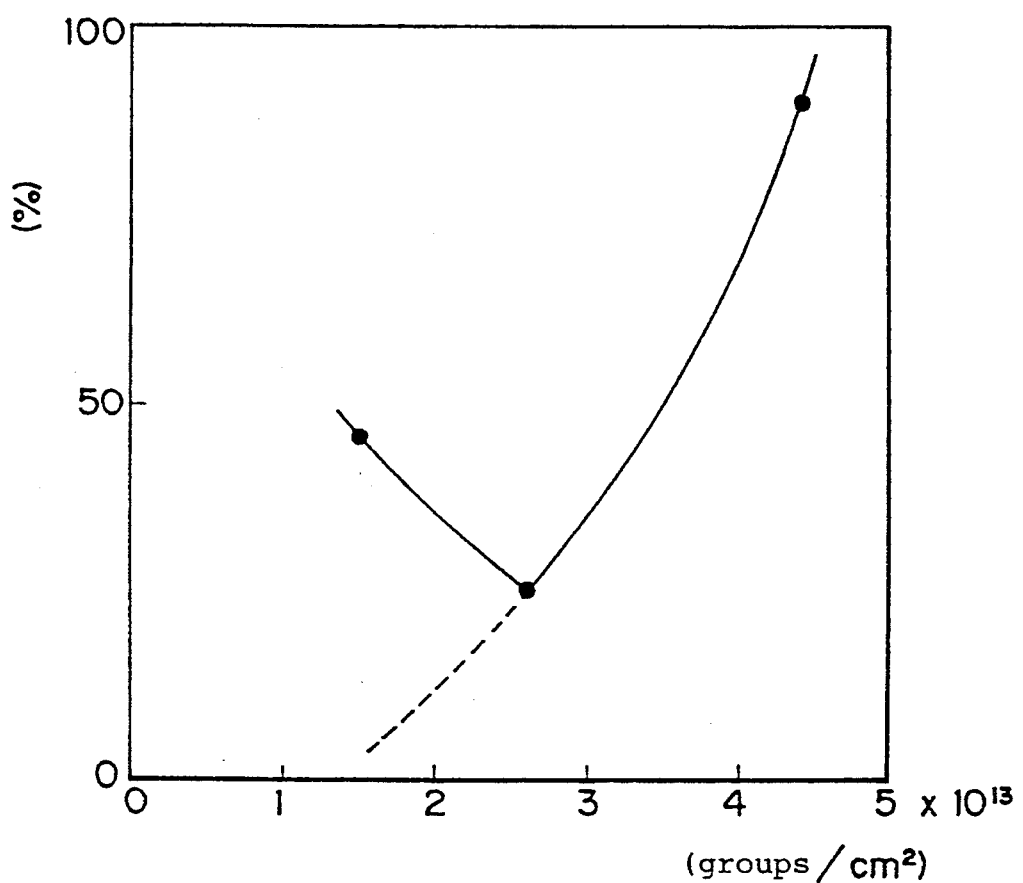
FIG. 7 shows the relationship between light transmittance of a fiber optics made of a polymethyl methacrylate and density of formyl groups. The axis of abscissa indicates number of formyl groups (groups/cm$^2$) and the axis of ordinate indicates light transmittance loss of the fiber FIG. 8 (a) shows the standard curve of the sandwich method.
Figure 8:
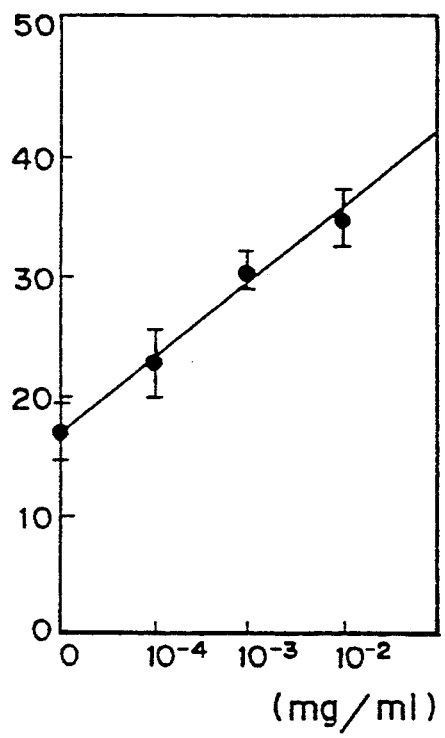
FIG. 8(b) shows that of the competitive format assay. The axis of abscissa indicates concentration of anti-mouse IgG (mg/ml), and the axis of ordinate indicates count number.
Figure 8:
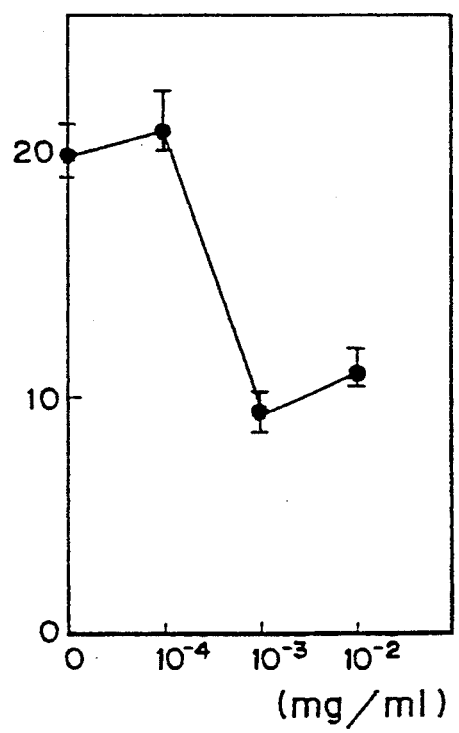
Figure 9:
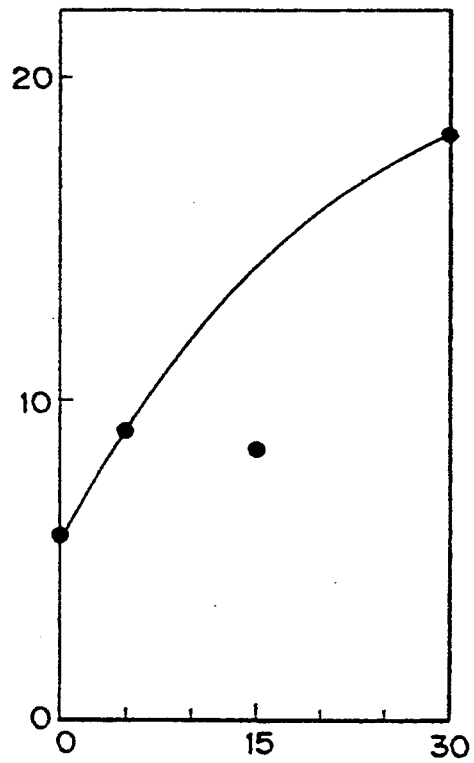
FIG. 9 shows response to sensor. The axis of abscissa indicates dipping time (min) into anti-mouse IgG ($10^{-3}$ mg/ml), and the axis of ordinate indicates count number. 1 is a fiber optics, 2: a clad layer, 3: a core surface, 4: an antigen, 5: a flow cell, Y: a fluorescence labelled antibody of the present invention, Y: an antibody in sample, 6: a He-Ne laser generating device or a laser generating device having a semiconductor laser and an SHG device in combination, 7: a filter, 8: a spectrofluorophotometer, 9: a sensing chip, 10: a plate, 11: a guide rail for optical axis matching, 12: a mirror and 13: a half mirror.

We claim:

1. A biomaterials assay device, comprising a light source, an optical fiber for transmitting an exciting light or a fluorescent light, and a sensing portion having a core surface and removably connected with said optical fiber, said sensing portion and said optical fiber being made of plastic selected from the group consisting of a polyacrylate, a polymethacrylate and a polyester having an ester structure and combinations thereof, said sensing portion having a substance specifically binding with an analyte immobilized on the core surface on one end of said sensing portion through a nucleophilic reagent having a formyl group represented by the formula:

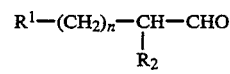

wherein R$^1$ and R$^2$ each represent a hydrogen atom, an alkyl group or a formyl group, and n represents an integer of 0 to 5, which reacts with the ester structure of said core surface; a filter for passing through only fluorescence excited at the sensing portion; and a photocounter for measuring an intensity of the fluorescence excited at the sensing portion.

2. In an optical fiber for use in an assay for biomaterials, wherein the improvement comprises a sensing portion removably connected to said optical fiber, said sensing portion having a core surface, said optical fiber and said sensing portion each comprises a plastic having an ester structure, said ester structure of said sensing portion being bonded with a nucleophilic reagent having a formyl group represented by the formula:

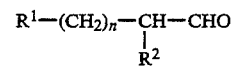

wherein R$^1$ and R$^2$ each represents a hydrogen atom, an akyl group or a fonnyl group, and n represents an integer of 0 to 5, said formyl group of said nucleophilic reagent covalently bonding with a substance which specifically binds with a reagent for use in an assay for biomaterials.

3. The optical fiber according to claim 2, wherein a density of said formyl group is $1.0 \times 10^{10}$ to $6.0 \times 10^{13}$ groups/cm$^2$.

4. The optical fiber according to claim 2, wherein said plastic optical fiber is composed of at least one of acrylic and methacrylic ester resin.

5. The optical fiber according to claim 2, wherein the nucleophilic reagent having the formyl group is a dialdehyde.

6. The optical fiber according to claim 5, wherein the nucleophilic reagent having the formyl groups is a compound selected from the group consisting of glutaraldehyde, succinic dialdehyde and adipoaldehyde.

7. The optical fiber according to claim 2, wherein the plastic is a polyacrylate or a polyester.

8. The optical fiber according to claim 7, wherein the plastic is a polyacrylate comprising at least one of methyl acrylate, ethyl acrylate and methyl methacrylate or a polyester.

9. In a sensing portion of a biomaterial assay device containing an optical fiber and said sensing portion for use in an assay for biomaterials, wherein the improvement comprises said sensing portion having a core surface to which is bound a nucleophilic reagent having formyl groups and a substance which specifically binds with an analyte covalently bonded to said formyl groups, said optical fiber and said sensing portion each comprises plastic having an ester structure, said nucleophilic reagent having said formyl groups being bonded with the ester structure of the sensing portion, said formyl groups of said nucleophilic reagent represented by the formula:

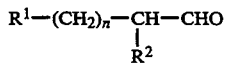

wherein $R^1$ and $R^2$ each represents a hydrogen atom, an alkyl group or a formyl group, and n represents an integer of 0 to 5.

10. A biomaterial assay device comprising:
   a light source (6),
   a plastic optical fiber (1) for transmitting an exciting light or a fluorescent light,
   a sensing portion (9) made of plastic having an ester structure and having a substance (4) which specifically binds with an analyte immobilized on a core surface of one end of an exposed area of said sensing portion (9) through a nucleophilic reagent having formyl groups represented by the formula:

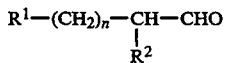

wherein $R^1$ and $R^2$ each represents a hydrogen atom, an akyl group or a formyl group, and n represents an integer of 0 to 5, which binds with said ester structure of said sensing portion;
   a filter (7) for only passing through the fluorescence excited at the sensing portion (9);
   a photocounter (8) for measuring an intensity of the fluorescence excited at the sensing portion (9);
   a guide rail (11) positioned along longitudinal edge surfaces of the optical fiber (1) and
   the sensing portion (9) removably connected to said optical fiber (1) along with guide rail (11).

11. The device according to claim 10, wherein said light source is a semiconductor laser.

12. The device according to claim 10, wherein said sensing portion is an opposing type.

13. The device according to claim 10, wherein said optical fiber and said sensing portion each comprises a polyacrylate or a polyester resin having an ester structure and said nucleophilic reagent bonded to the resin of said sensing portion through said ester structure, said nucleophilic reagent having formyl groups which covalently bond with a substance which binds with a reagent for use in a biomaterial assay.

14. The biomaterials assay device according to claim 10, wherein the sensing portion and the optical fiber are made of plastic having an ester structure selected from the group consisting of a polyacrylate, a polymethacrylate, a polyester and combination thereof, said formyl groups of said nucleophilic reagent binds with the ester structure of said core surface of the sensing portion, and a substance which binds with an analyte covalently bonded to said formyl groups of the nucleophilic reagent, 15. The device according to claim 10, wherein the plastic is a polyacrylate or a polyester.

16. The device according to claim 15, wherein the polyacrylate is selected from the group consisting of methyl acrylate, ethyl acrylate, methyl methacrylate and combinations thereof.

* * * * *